(12) United States Patent
Lin

(10) Patent No.: US 11,872,466 B2
(45) Date of Patent: Jan. 16, 2024

(54) REHABILITATION ACTION GUIDANCE ASSISTIVE DEVICE

(71) Applicant: New Century Products Limited, Taipei (TW)

(72) Inventor: Fu-Tsun Lin, Taipei (TW)

(73) Assignee: NEW CENTURY PRODUCTS LIMITED, Taipei (TW)

( * ) Notice: Subject to any disclaimer, the term of this patent is extended or adjusted under 35 U.S.C. 154(b) by 32 days.

(21) Appl. No.: 17/577,379

(22) Filed: Jan. 18, 2022

(65) Prior Publication Data

US 2023/0226430 A1 Jul. 20, 2023

(51) Int. Cl.
*A63B 24/00* (2006.01)
*A63B 71/06* (2006.01)
*G08B 5/22* (2006.01)
*H04W 4/80* (2018.01)

(52) U.S. Cl.
CPC ...... *A63B 71/0622* (2013.01); *A63B 24/0075* (2013.01); *G08B 5/22* (2013.01); *A63B 2071/065* (2013.01); *A63B 2071/0625* (2013.01); *A63B 2071/0655* (2013.01); *A63B 2220/17* (2013.01); *A63B 2220/34* (2013.01); *A63B 2220/40* (2013.01); *A63B 2220/62* (2013.01); *A63B 2225/54* (2013.01); *H04W 4/80* (2018.02)

(58) Field of Classification Search
CPC ............ A63B 71/0622; A63B 24/0075; A63B 2071/0625; A63B 2071/065; A63B 2071/0655; A63B 2220/17; A63B 2220/34; A63B 2220/40; A63B 2220/62; A63B 2225/54; G08B 5/22; H04W 4/80
See application file for complete search history.

(56) References Cited

U.S. PATENT DOCUMENTS

2017/0095693 A1* 4/2017 Chang .................... G16H 40/40

* cited by examiner

*Primary Examiner* — Robert P Bullington, Esq.
(74) *Attorney, Agent, or Firm* — Leong C. Lei

(57) ABSTRACT

The present invention provides a rehabilitation action guidance assistive device comprising a display device, a sensing device and a rehabilitation evaluation system. The display device displays an image for a user to watch and imitate. The sensing device comprises a sensing element, a storage element, a processing element, a data transmission element and a power supply element. The sensing element is used for sensing action state values of the rehabilitation carrier or the user; the storage element is used for storing the action state values; the processing element is used for performing a signal calculation; the data transmission element transmits the action state values to the rehabilitation evaluation system through a wireless communication method; and the power supply element provides an electric power to the sensing device. The rehabilitation evaluation system indicates the difference in ratio between the user's action state values and reference action state values.

6 Claims, 13 Drawing Sheets

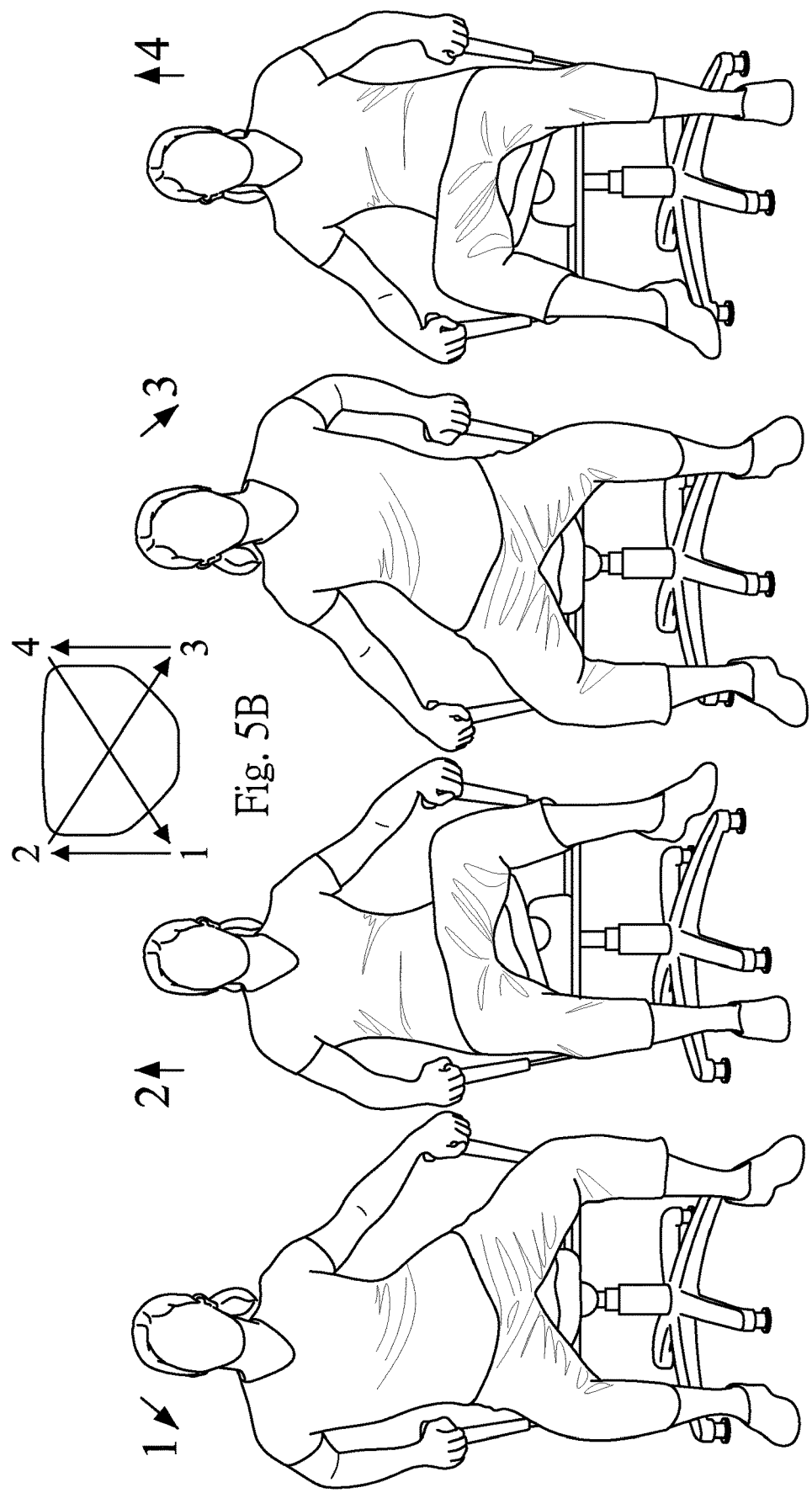

REHABILITATION ACTION GUIDANCE ASSISTIVE DEVICE

TECHNICAL FIELD OF THE INVENTION

The present invention relates to a rehabilitation action guidance assistive device, and more particularly to a rehabilitation action guidance assistive device to relieve or alleviate the discomfort of muscles and bones in the lumbar, cervical, shoulder, foot joints or other parts of the body.

DESCRIPTION OF THE PRIOR ART

With the advancement in technology and the continuous development of industry and commerce, people need to sit and work for a long time. Whether they are working on a production line or doing business tasks in the office, it is possible to accumulate excessive stress on the muscles and bones due to maintaining the same fixed posture for a long time, resulting in various kinds of muscle and bone problems. The most common type of pain in musculoskeletal disorders caused by sitting is pain in the lower back, followed by pain in the neck and shoulders. Furthermore, sitting for long periods of time can easily lead to muscle tightness or weakness in the joints of the feet.

The angle between the trunk and the thigh is 90 degrees when we sit down. Because the thigh rotates 90 degrees to the pelvis, the buttock muscles connecting the pelvis, the thigh, and the hamstrings on the back of the thigh to the thigh bone are stretched due to the influence of the rotation, causing the pelvis to rotate backward, which can easily straighten the curvature of the lumbar vertebrae. The weight of the thoracic cavity needs to be equally distributed by the waist and abdomen to maintain the stability of the thoracic cavity directly above the pelvis when sitting. If the waist muscles are not developed and cannot bear excessive weight of the thoracic cavity, it will result in the lumbar vertebrae bearing the weight of the thoracic cavity instead. A discomfort of the sedentary behavior can be improved and relieved by a massage, pain relief patches, or traditional Chinese medicine, etc., but back pain and spinal degeneration can never be treated or prevented from worsening. In addition, as such treatments cannot be performed at home, people need to go to rehabilitation hospitals or physical therapy centers multiple times which leads to prolonged recovery period.

In order to solve the problem mentioned above, the inventor has invested in a lot of research, development, and effort in making breakthroughs and innovations, hoping to solve the current shortcomings with novel technical methods, not only bringing better products to the society, but also promoting industrial development at the same time.

SUMMARY OF THE INVENTION

In view of the aforementioned problems of sedentary behavior, the muscles and bones of the lumbar vertebrae, cervical spine, shoulders, foot joints and other parts are uncomfortable. The main purpose of the present invention is to provide a rehabilitation action guidance assistive device, the usage of which is not restricted by location and can be operated-independently without danger during use, so that the physiological curvature of the lumbar, cervical or thoracic spine can be restored through the rehabilitation action guidance assistive device.

To achieve the above objective, the present invention provides a rehabilitation action guidance assistive device comprising a display device, a sensing device and a rehabilitation evaluation system; wherein the display device has a user interface that displays an image for a user to watch, and the image is a demonstration of rehabilitation actions and a model portrait that the user can imitate. Further, the sensing device is disposed on the rehabilitation carrier or the user, and the sensing device comprises a sensing element, a storage element, a processing element, a data transmission element and a power supply element; wherein the sensing element is an inertial measurement unit and used for sensing action state values of the rehabilitation carrier or the user; the storage element installed in the sensing device is electrically connected to the sensing elements and used for storing the action state values sensed by the sensing elements; the processing element is installed in the sensing device and is electrically connected to the storage element for receiving the action state values stored in the storage element to perform a signal calculation, and then compared with a preset value to determine whether to generate a warning signal or not; the data transmission element is installed in the sensing device and is electrically connected to the processing element and transmits the action state values to the rehabilitation evaluation system through a wireless communication method; and the power supply element is installed in the sensing device and is electrically connected to the sensing elements, the storage element, the processing element and the data transmission element, so as to provide an electric power with an operational function of the sensing device. Moreover, the rehabilitation evaluation system is installed in the display device and indicates the difference in ratio between the user's action state values and reference action state values of the model portrait.

In some embodiments, the action state values are acceleration values, rotation angular velocity values of the rehabilitation carrier or the user, or a linear velocity of carriers or body parts after the signal calculation based on the acceleration value and the rotation angular velocity value, positions of the carriers or body parts or posture angles of the carriers or body parts.

In some embodiments, the action state values and the reference action state values are a sequence of numbers of X-axis, Y-axis and Z-axis represented by a time series sequence, X-axis is the left and right direction relative to the human body, Y-axis is the front and back direction relative to the human body, Z-axis is the up and down direction of the human body. The following error value of the time series sequence is calculated, an error angle value is calculated through the calculation of trigonometric function equation, and an average error angle is obtained.

In some embodiments, when the average error angle is less than 10 degrees, it means that the user's rehabilitation action is correct; when the average error angle is between 10 degrees and 20 degrees, it means that the user's rehabilitation action is acceptable; and when the average error angle is between 20 degrees and 30 degrees, it means that the user's rehabilitation action needs to be reviewed and corrected.

In some embodiments, the inertial measurement unit is a triaxial accelerometer, a combination of a three-axis gyro and the triaxial accelerometer, or a combination of the three-axis gyro, the triaxial accelerometer and a three-axis geomagnetometer.

In some embodiments, when the processing element determines that a warning signal needs to be sent out, it triggers a warning element to send out the warning signal. Simultaneously, the data transmission element sends the warning signal to the display device so that the user interface displays the warning signal. Further, the warning element is a buzzer or a vibrator.

In some embodiments, the processing element further comprises a timer and a counter; wherein the timer is used for calculating a time length when the sensing element is operated; and the sensing element transmits swing signals from the rehabilitation carrier or the user to the counter, so that the counter records the swing signals of the rehabilitation carrier or the user as a frequency signal. Furthermore, the time length and the frequency signal are transmitted to the storage element, and the time length and the frequency signal are transmitted to the display device through the processing element and the data transmission element.

In some embodiments, the wireless communication method is one of BLUETOOTH® communication protocol, wireless network communication protocol, wireless RF communication, broadband network communication, ZIGBEE®, THREAD®, 3G® communication protocol or 4G® communication protocol.

In some embodiments, the rehabilitation action guidance assistive device is a lumbar spine swing rehabilitation chair, a somatic stretching core muscle training device, a cervical spine stretching rehabilitation device or a leg joint rehabilitation belt.

BRIEF DESCRIPTION OF THE DRAWINGS

The above and other objects, features, and other advantages of the present invention will be more clearly understood from the following detailed description taken in conjunction with the accompanying drawings, in which:

FIG. 5B-FIG. 5F are schematic views of the use of the lumbar spine swing rehabilitation chair according to embodiment 1 of the present invention;

DETAILED DESCRIPTION OF THE PREFERRED EMBODIMENTS

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

The term "connection" as used herein may refer to electrical connection or communication connection, depending on the context; wherein the communication connection may include wired communication and wireless communication. The wired communication includes but is not limited to a wired network or a direct telecommunications connection. Communication includes but is not limited to sound wave, infrared, radio, electromagnetic wave, spread spectrum technology, or other wireless communication technology.

Figure 1A:
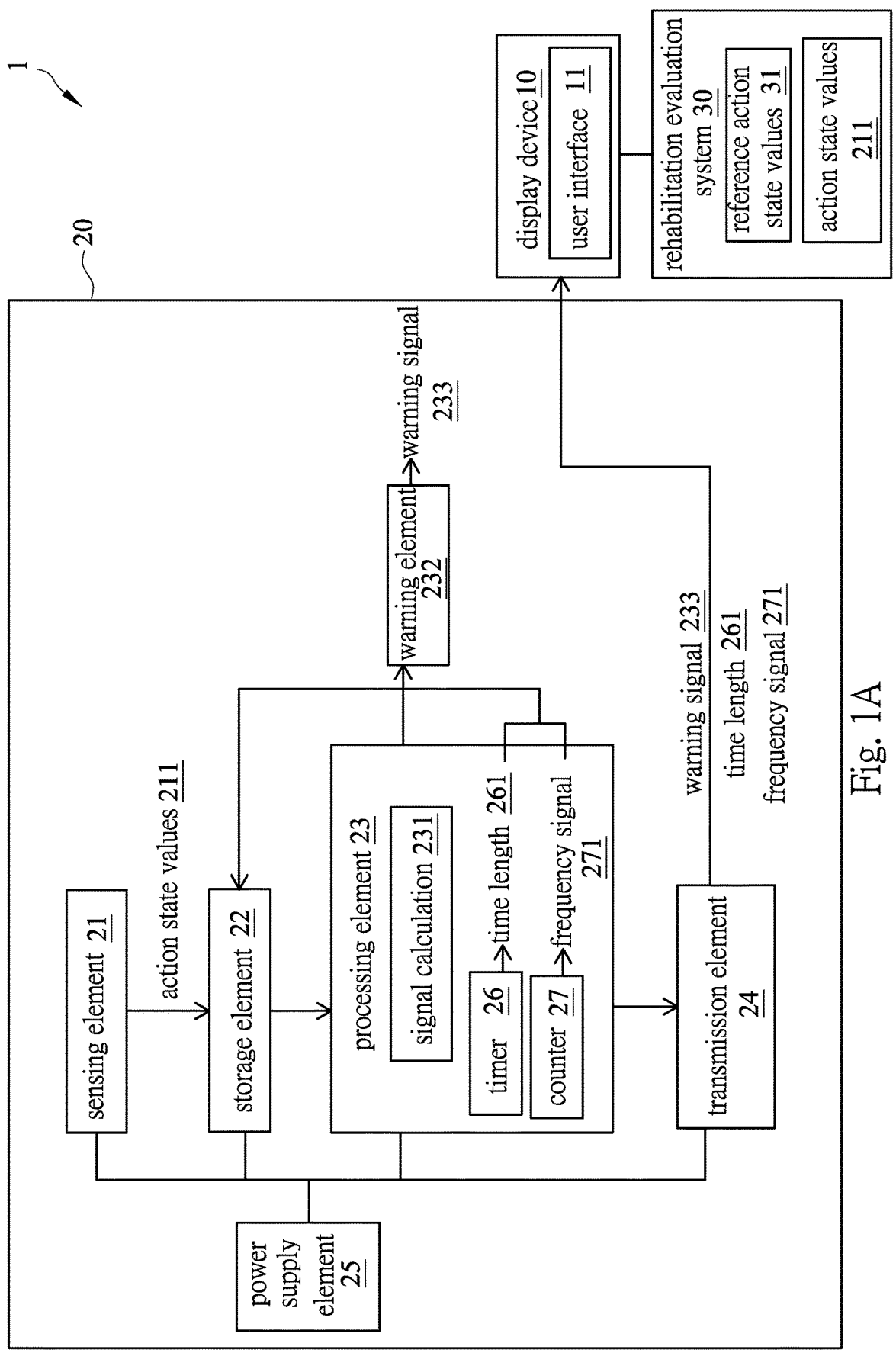
FIG. 1A is a schematic view of a rehabilitation action guidance assist device of the present invention.

Please refer to FIG. 1A, FIG. 1A is a schematic view of a rehabilitation action guidance assistive device of the present invention.

As shown in FIG. 1A, the present invention provides a rehabilitation action guidance assist device 1 comprising a display device 10, a sensing device 20 and a rehabilitation evaluation system 30; wherein the display device 10 has a user interface 11 that displays an image for a user to watch, and the image is a demonstration of rehabilitation actions and a model portrait that the user can imitate. Further, the sensing device 20 is disposed on the rehabilitation carrier or the user, and the sensing device 20 comprises a sensing element 21, a storage element 22, a processing element 23, a data transmission element 24 and a power supply element 25. Further, the sensing element 21 is an inertial measurement unit and used for sensing action state values 21 of the rehabilitation carrier or the user; and the storage element 22 installed in the sensing device 20 is electrically connected to the sensing elements 21, and is used for storing the action state values 211 sensed by the sensing elements 21. Furthermore, the processing element 23 is installed in the sensing device 20 and is electrically connected to the storage element 22 for receiving the action state values 211 stored in the storage element 22 to perform a signal calculation, and then compare with a preset value to determine whether to generate a warning signal 233 or not; when the processing element 23 determines that a warning signal 233 needs to be sent out, it triggers a warning element 232 to send out the warning signal 233. Simultaneously, the data transmission element 24 sends the warning signal 233 to the display device 10 so that the user interface 11 displays the warning signal 233. Further, the warning element 232 is a buzzer or a vibrator. Moreover, the processing element 23 further comprises a timer 26 and a counter 27; wherein the timer 26 is used for calculating a time length 261 when the sensing element 21 is operated; and the sensing element 21 transmits swing signals from the rehabilitation carrier or the user to the counter 26, so that the counter 26 records the swing signals of the rehabilitation carrier or the user as a frequency signal 271. Furthermore, the time length 261 and the frequency signal 271 are transmitted to the storage element 22, and the time length 261 and the frequency signal 271 are transmitted to the display device 30 through the processing element 23 and the data transmission element 24. In addition, the data transmission element 24 is installed in the sensing device 20 and is electrically connected to the processing element 23 and transmits the action state values 211 to the display device 10 through a wireless communication method; and the power supply element 25 is installed in the sensing device 20 and is electrically connected to the sensing elements 21, the storage element 22, the processing element 23 and the data transmission element 24, so as to provide an electric power with an operational function of the sensing device 20.

Figure 1B:
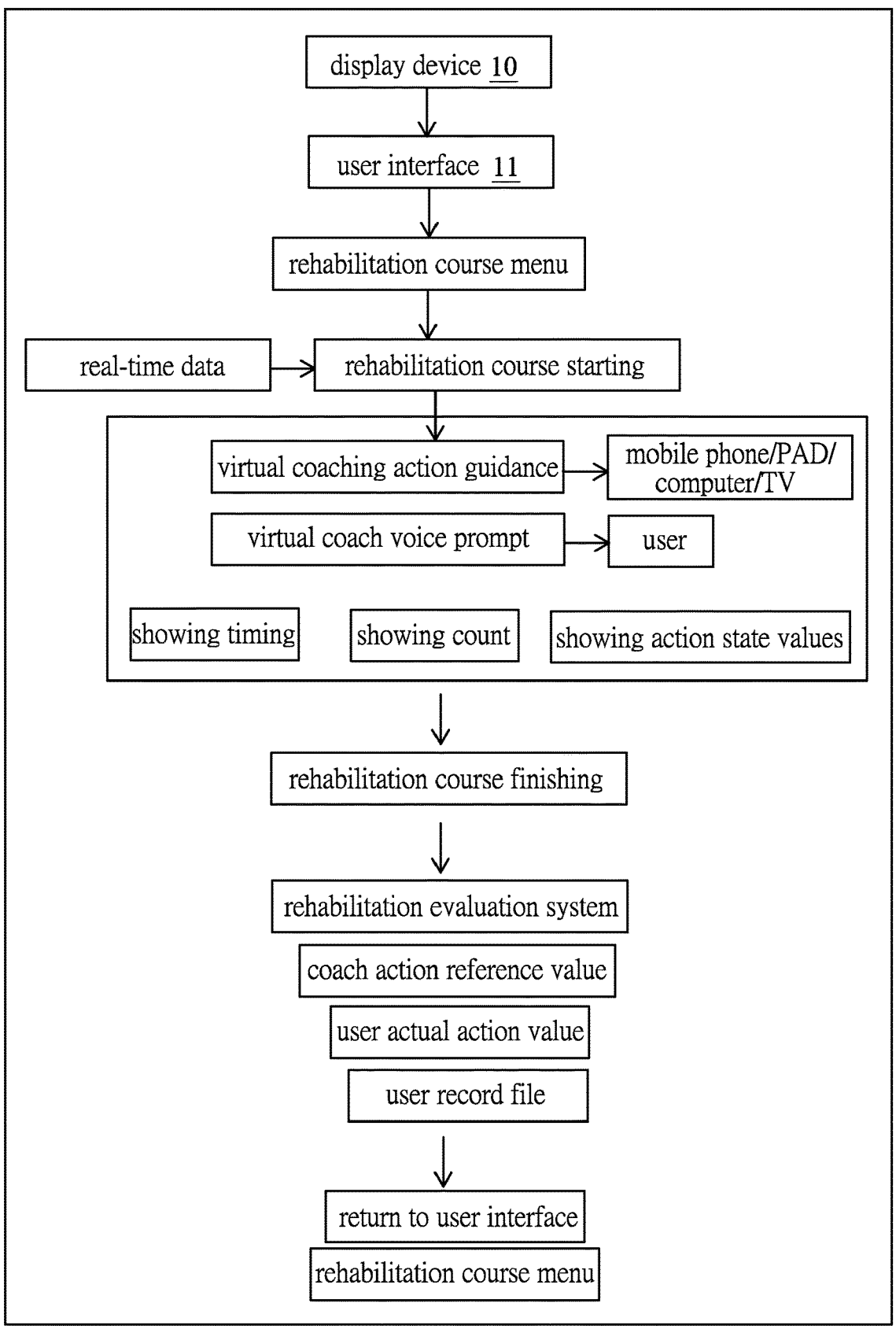
FIG. 1B is a flow chart of a user operating on the display device of the present invention.
Figure 2:
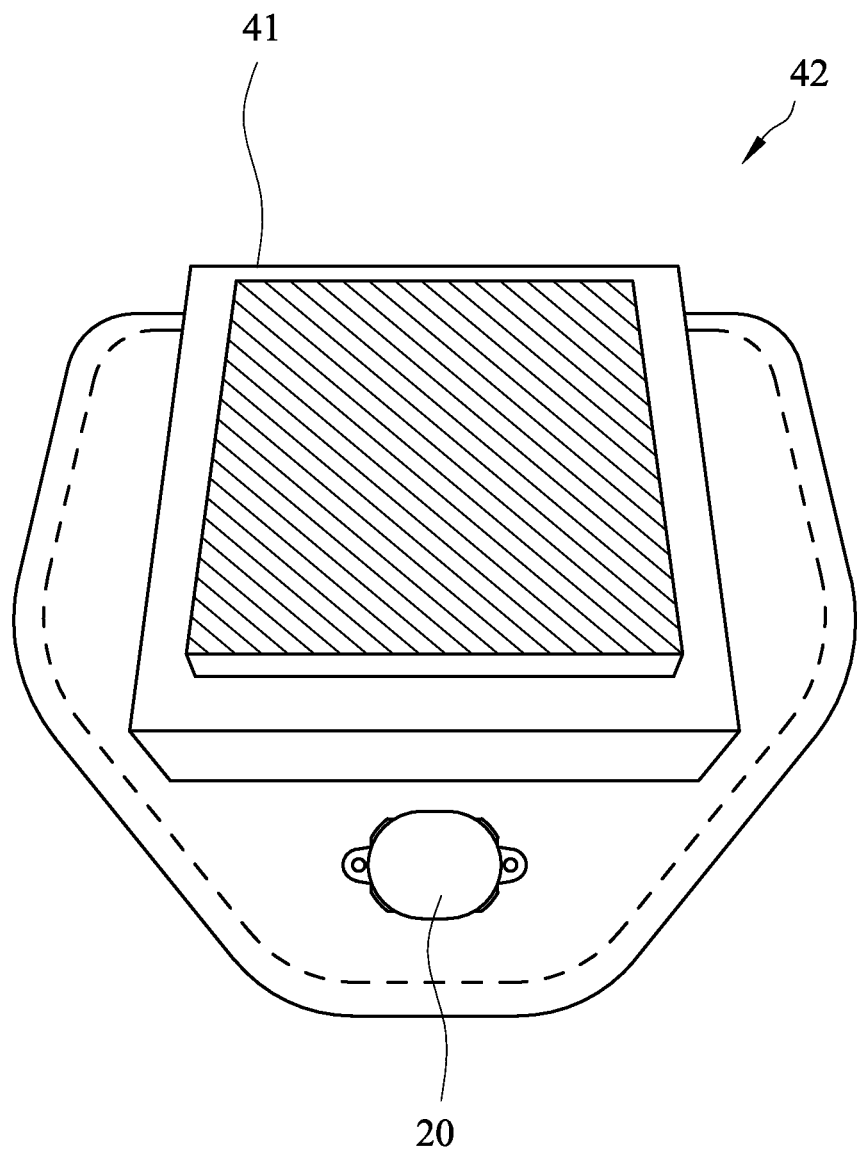
FIG. 2 is a schematic view of a back of a chair cushion of a lumbar spine swing rehabilitation chair according to the first embodiment of the present invention.

Please refer to FIG. 1B, FIG. 1B is a flow chart of a user operating on the display device of the present invention.

As shown in FIG. 1B, the user clicks on a rehabilitation course menu on the user interface 11 of the display device 10 to open the selected rehabilitation course. The display device 10 also receives the real-time data of the sensing device 20, and the display device 10 displays a virtual coach action guidance and generates a virtual coach voice prompt to remind the user. Further, the rehabilitation evaluation system 30 displays time, frequency and action state values. After the rehabilitation course is over, the rehabilitation evaluation system 30 only displays the degree of difference between the user's action state values (that is, the user's actual action value) and a reference action state values (that is, the coach action reference value) of the model portrait, and a user record file is generated. The user can return to the rehabilitation course menu on the user interface 11 and perform other rehabilitation.

The inertial measurement unit is a triaxial accelerometer, a combination of a three-axis gyro and the triaxial accelerometer, or a combination of the three-axis gyro, the triaxial accelerometer and a three-axis geomagnetometer. Further, the wireless communication method is one of BLUETOOTH® communication protocol, wireless network communication protocol, wireless RF communication, broadband network communication, ZIGBEE®, THREAD®, 3G® communication protocol or 4G® communication protocol. Furthermore, the display device 10 can be a computer device, a mobile phone device, a television screen, a tablet computer device or an electronic device that can be monitored in real time, but the present invention is not limited thereto.

Figure 3:
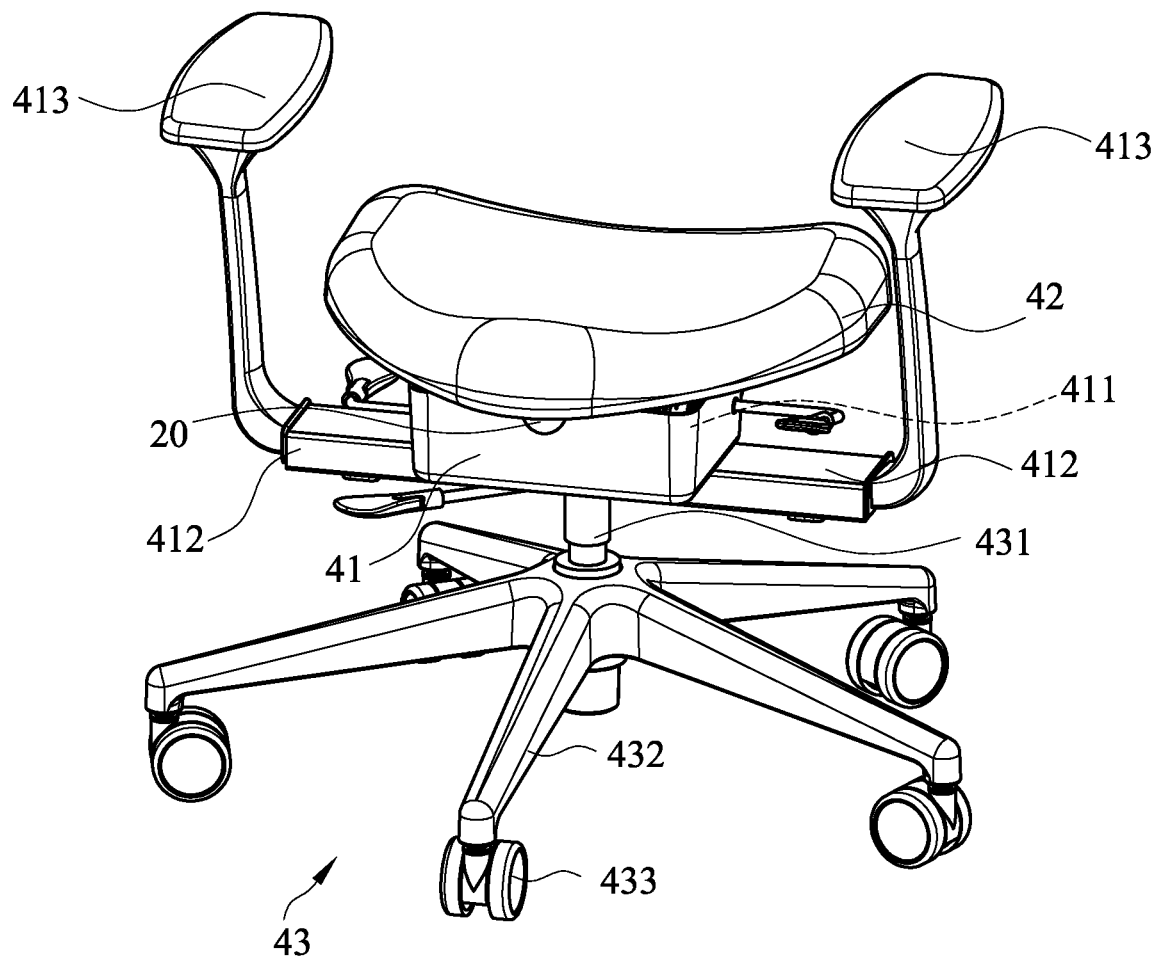
FIG. 3 is a stereoscopic schematic diagram of the lumbar spine swing rehabilitation chair according to embodiment 1 of the present invention.
Figure 4:
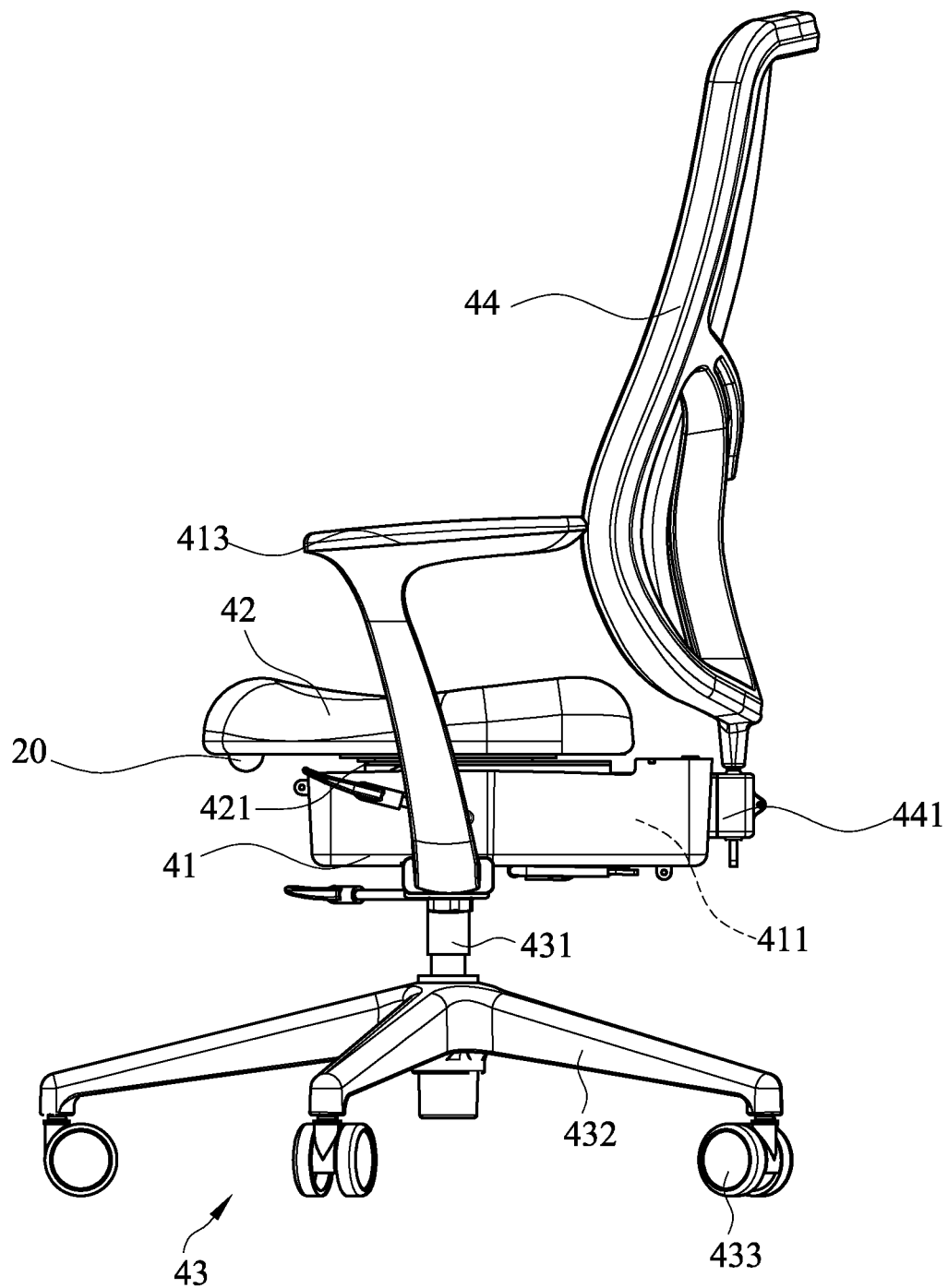
FIG. 4 is a side view of the lumbar spine swing rehabilitation chair according to embodiment 1 of the present invention.
Figure 5A:
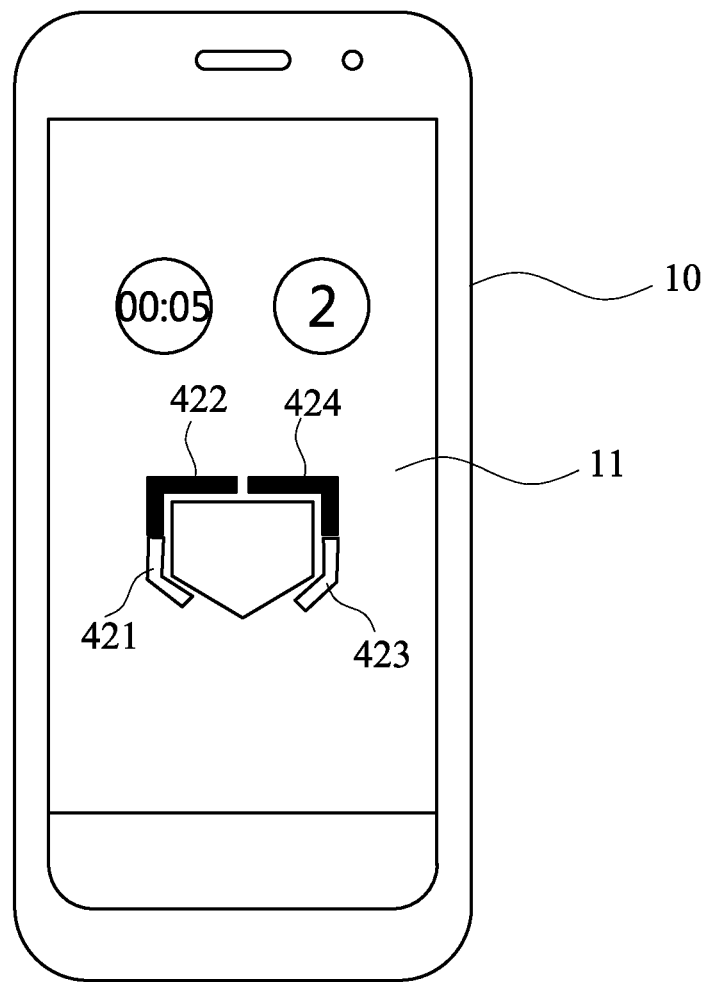
FIG. 5A is a schematic view of a display device of the lumbar spine swing rehabilitation chair according to embodiment 1 of the present invention.
Figure 6A:
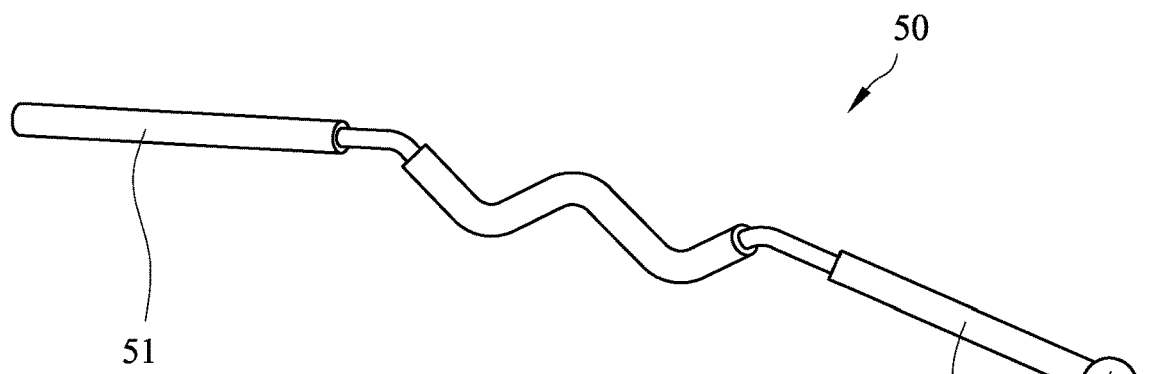
FIG. 6A is a schematic view of a somatic stretching core muscle training device according to embodiment 2 of the present invention.
Figure 6B:
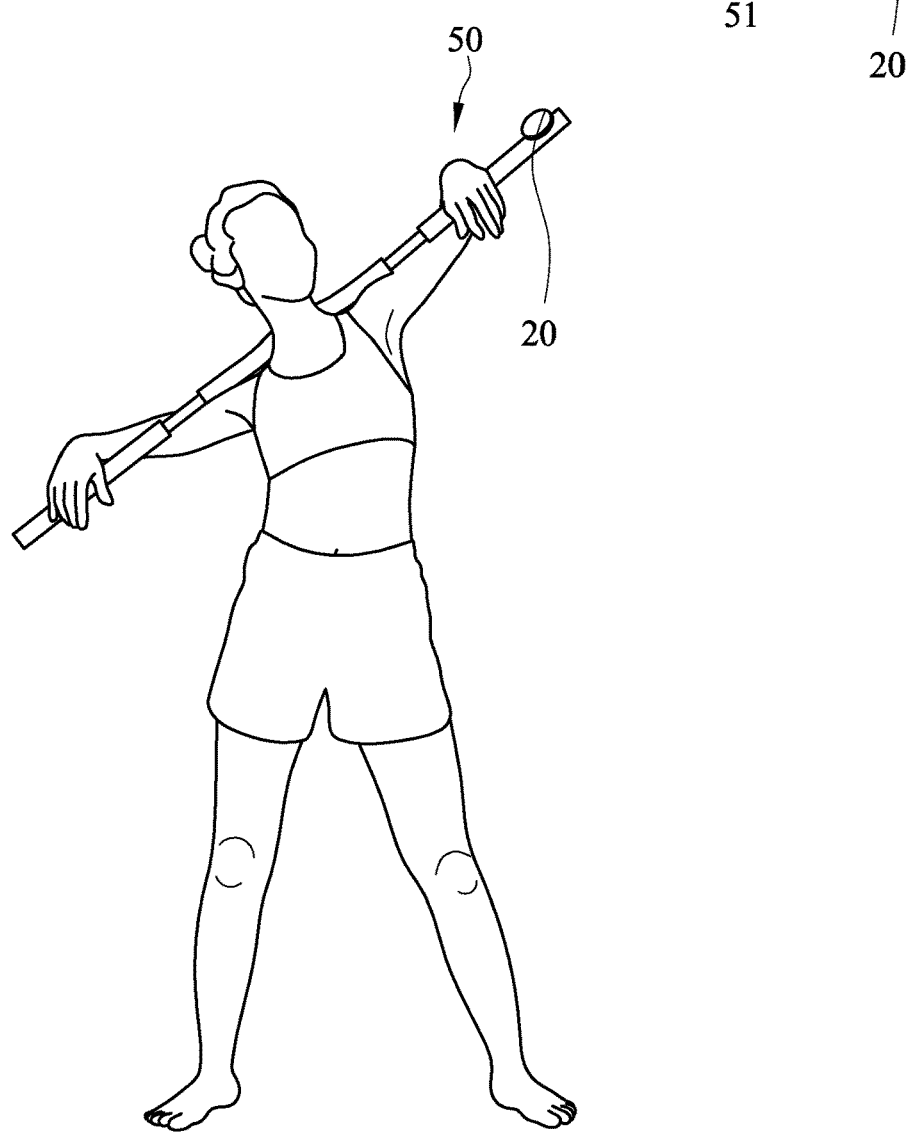
FIG. 6B-FIG. 6G are schematic views of the use of the somatic stretching core muscle training device according to embodiment 2 of the present invention.
Figures 6C, 6D, 6E:
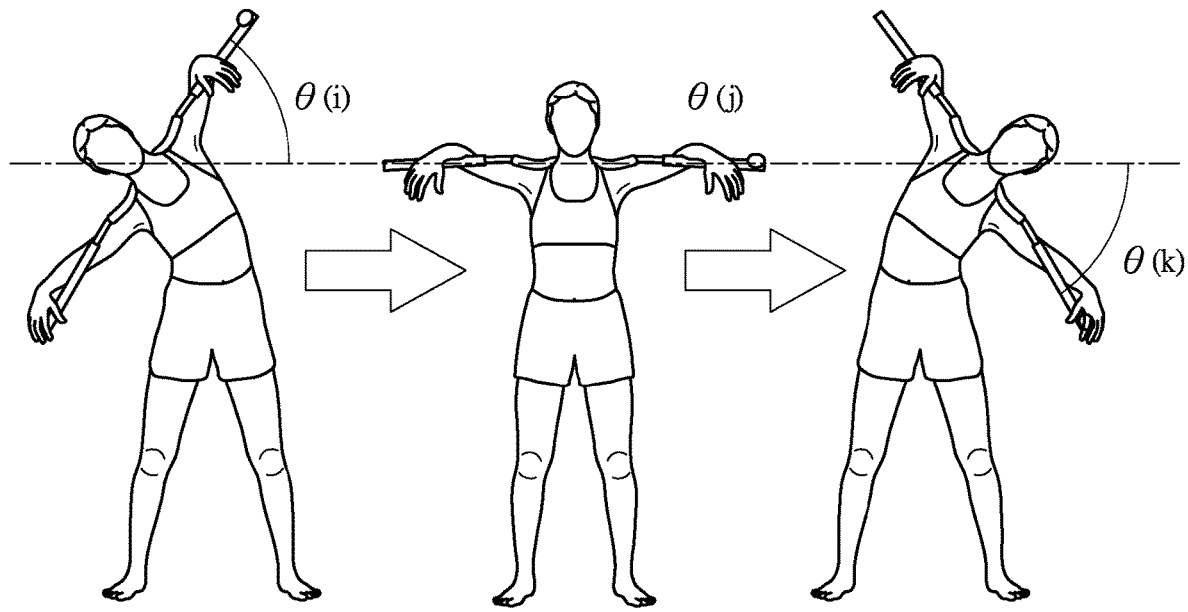
Figures 6F, 6G:
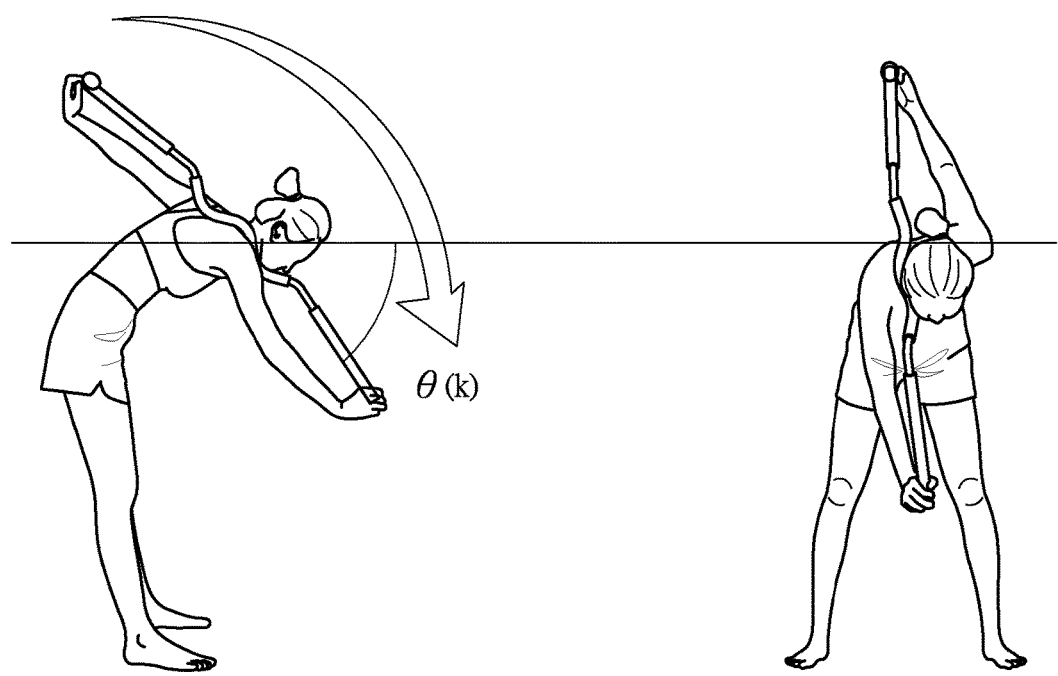

Please refer to FIG. 2 to FIG. 5F, FIG. 2 is a schematic view of a back of a chair cushion of a lumbar spine swing rehabilitation chair according to the first embodiment of the present invention; FIG. 3 is a stereoscopic schematic diagram of the lumbar spine swing rehabilitation chair according to embodiment 1 of the present invention; FIG. 4 is a side view of the lumbar spine swing rehabilitation chair according to embodiment 1 of the present invention; FIG. 5A is a schematic view of a display device of the lumbar spine swing rehabilitation chair according to embodiment 1 of the present invention; and FIG. 5B-FIG. 5F are schematic views of the use of the lumbar spine swing rehabilitation chair according to embodiment 1 of the present invention.

As shown in FIG. 1 to FIG. 5F, the rehabilitation action guidance assistive device 1 is a lumbar spine swing rehabilitation chair 40 comprising a support base 41, a seat cushion 42, the sensing device 20, a chair foot base 43, and a chair back 44; wherein the support base 41 has an accommodating space 411, and two cross bars 412 are provided on both sides of the bottom of the support base 41, and the two cross bars 412 have a pair of armrests 413 extending upward. Further, the seat cushion 42 is swingably disposed on the support base 41 by a connecting mechanism 421, and the connecting mechanism 421 is installed in the accommodating space 411. In addition, the sensing device 20 is disposed under the seat cushion 42, and the sensing element 21 is used for sensing the action state values 211 of the seat cushion 42 or the user; wherein the action state values 211 are acceleration values, rotation angular velocity values of the lumbar spine swing rehabilitation chair 40 or the user, or a linear velocity of body parts after the signal calculation based on the acceleration value and the rotation angular velocity value, positions of the body parts or posture angles of the body parts. Furthermore, the storage element 22 is used for storing the action state values 211 sensed by the sensing elements; the processing element 23 is used for receiving the action state values 211 to perform a signal calculation 231, and then compared with a preset value to determine whether to generate a warning signal 233 or not. Moreover, the data transmission element 24 transmits the action state values 211 to the display device 10 through a wireless communication method, and the rehabilitation evaluation system 30 is installed in the display device 10 and power supply element 25 provides an electric power with an operational function of the sensing device 20. The processing element 23 further comprises a timer 26 and a counter 27; wherein the timer 26 is used for calculating a time length when the sensing element is operated; and the sensing element 21 transmits swing signals from the rehabilitation carrier or the user to the counter, so that the counter 26 records the swing signals of the rehabilitation carrier or the user as a frequency signal 271. Furthermore, the time length 261 and the frequency signal 271 are transmitted to the storage element 22, and the time length 261 and the frequency signal 271 are transmitted to the display device 10 through the processing element 23 and the data transmission element 24. Moreover, the chair foot base 43 is connected to the support base 41 through a connecting rod 431; the chair foot base 43 has a plurality of legs 432 and a plurality of castors 433, and each leg 432 is provided with a castor 433; and the bottom of the chair back 44 is connected to the support base 41 by a coupling component 441.

As mentioned above, the action state values 211 and the reference action state values 31 are a sequence of numbers of X-axis, Y-axis and Z-axis represented by a time series sequence, X-axis is the left and right direction relative to the human body, Y-axis is the front and back direction relative to the human body, Z-axis is the up and down direction of the human body.

$[Gx(k)'Gy(k)'Gz(k)]_{ref}$, K=1 . . . n, it represents the reference action state values of the model portrait at Tk;

$[Gx(k)'Gy(k)'Gz(k)]_{act}$, K=1 . . . n, it represents the user's action state values at Tk.

The following error value of the time series sequence is calculated.

The following error value $(k)=\sqrt{[Gx(k)_{ref}-Gx(k)_{act}]^2+[Gy(k)_{ref}-Gy(k)_{act}]^2+[Gz(k)_{ref}-Gz(k)_{act}]^2}$;

an error angle value is calculated through the calculation of trigonometric function equation, and an average error angle is obtained;

ErrorAngle$(k)$=Error$(k)/G*(180/Pi)$

Average Error Angle=ΣError Angle$(k)/n$ k=1 . . . n;

wherein when the average error angle is less than 10 degrees, it means that the user's rehabilitation action is correct; when the average error angle is between 10 degrees and 20 degrees, it means that the user's rehabilitation action is acceptable; and when the average error angle is between 20 degrees and 30 degrees, it means that the user's rehabilitation action needs to be reviewed and corrected. Further, the rehabilitation evaluation system 30 not only informs the user of the correctness of the rehabilitation exercise, but also records the user's exercise data in a file for comparison and reference or exercise correction.

As shown in FIG. 3 to FIG. 5F, the inclination angle of the seat cushion 42 with respect to the support base 41 is between 40 and 50 degrees; and the connecting rod 431 is fixed between the support base 41 and the chair foot base 43. Furthermore, the connecting rod 431 is used as a rotation axis so that the seat cushion 42 swings in a 360-degree rotation range around the connecting rod 431. Therefore, the lumbar spine swing rehabilitation chair 40 can perform forward and backward movement, left and right movement, rotation and swing with the connecting rod 431 as a center of a 360° rotation range. The seat cushion 42 is similar to a pentagon; therefore, a pentagon on the sensing device 20 represents the seat cushion 42 and has four sensing blocks 421, 422, 423 and 424 showed on the edges of the pentagon. As shown in FIG. 5B to FIG. 5F, when the user sits on lumbar spine swing rehabilitation chair 40, the user leans in the direction of 1 to make the sensing block 421 on the a rehabilitation evaluation system 30 become black; the user leans in the direction of 2 to make the sensing block 422 on the a rehabilitation evaluation system 30 become black; the user leans in the direction of 3 to make the sensing block 423 on a rehabilitation evaluation system 30 become black; and the user leans in the direction of 4 to make the sensing block 424 on the a rehabilitation evaluation system 30 become black. Therefore, the user's swing times, swing time, and swing angle can be observed to confirm through the rehabilitation evaluation system 30 whether the user's swing times, time, and angle meet the requirements.

Please refer to FIG. 6A to FIG. 6G, FIG. 6A is a schematic view of a somatic stretching core muscle training device according to embodiment 2 of the present invention; and FIG. 6B-FIG. 6G are schematic views of the use of the somatic stretching core muscle training device according to embodiment 2 of the present invention.

As shown in FIG. 6A to FIG. 6G, Example 2 is substantially the same as Example 1, except that the rehabilitation carrier of Example 1 is the lumbar spine swing rehabilitation chair, and the rehabilitation carrier of Example 2 is a somatic stretching core muscle training device 50. In Example 2, the sensing device 20 is disposed on the end of the somatic stretching core muscle training device 50 to detect the direction and posture angle of the user's operation, and can also record the number of exercises, angles, time and date in real time. Further, put the somatic stretching core muscle training device 50 behind the user, and user's arms are placed on a cross bar 51 of the somatic stretching core muscle training device 50, so that the center of the cross bar 51 is placed on the neck of the user to form a straight line when viewed from the side. When the user expands his chest, the blade bone will open and become relaxed. Therefore, different parts of the body can be stretched by rotating the body at different angles, including shoulders, back, waist, and arms. As shown in FIG. 6C to FIG. 6G, $\theta_{(i)}$, $\theta_{(j)}$ and $\theta_{(k)}$ respectively represent the angles between the rehabilitation carrier and the left and right horizontal lines, and represent the left and right tilt angles of the user's body. Further, the front and back of $\theta_{(k)}$ represents the angle between the rehabilitation carrier and the front and back horizontal lines, and represents the angle of front and back bending of the user's body. Moreover, considering ergonomics and a reduction of burden on the body, the somatic stretching core muscle training device 50 has a special curve shape that fits the human body more closely, so that the users can do simple body stretching at home to relieve body soreness caused by daily housework and sedentary office work.

Figure 7A:
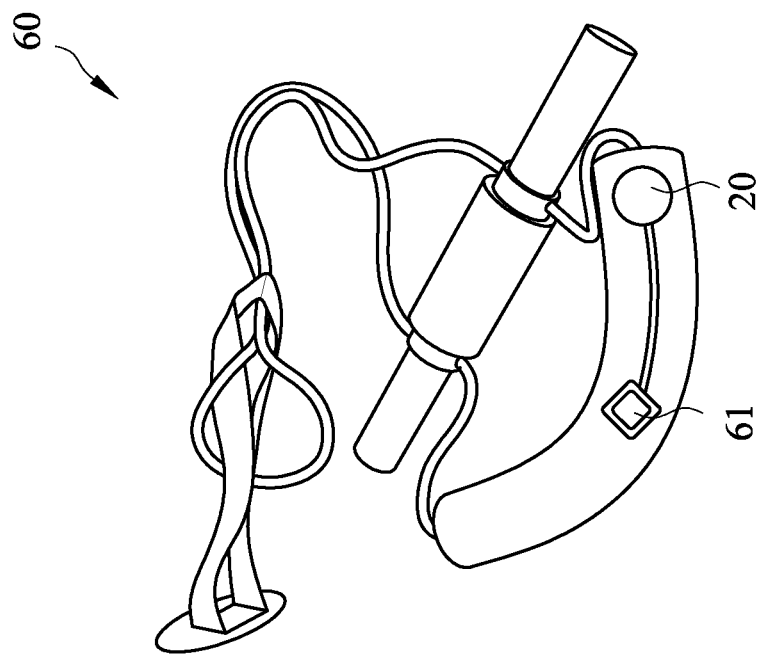
FIG. 7A is a schematic view of a cervical spine stretching rehabilitation device according to embodiment 3 of the present invention.
Figure 7C:
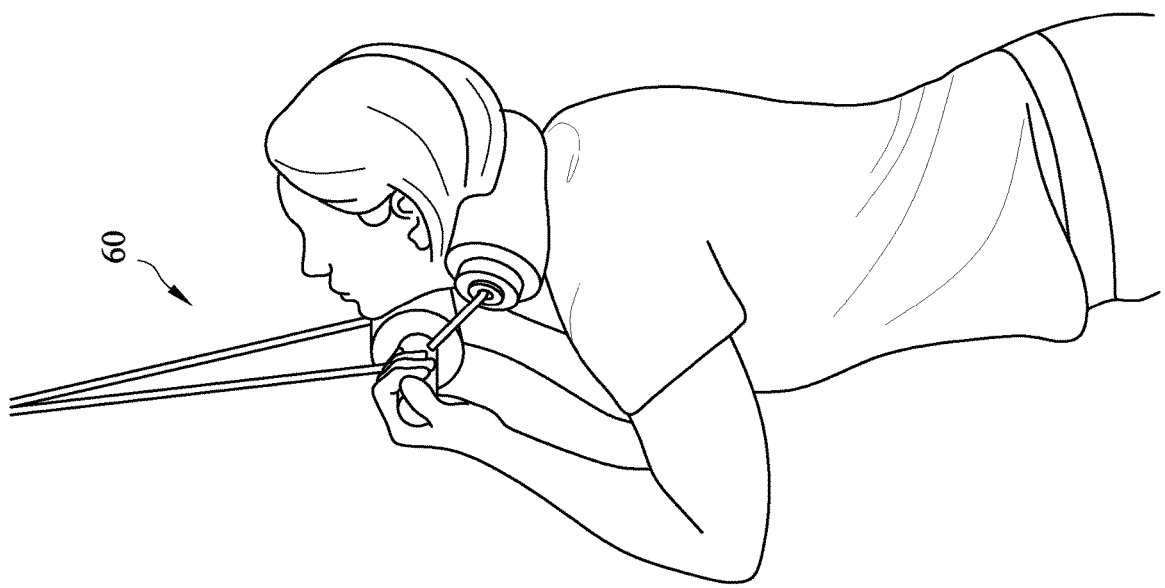
FIG. 7B-FIG. 7C are schematic views of the use of the cervical spine stretching rehabilitation device according to embodiment 3 of the present invention.
Figure 7B:
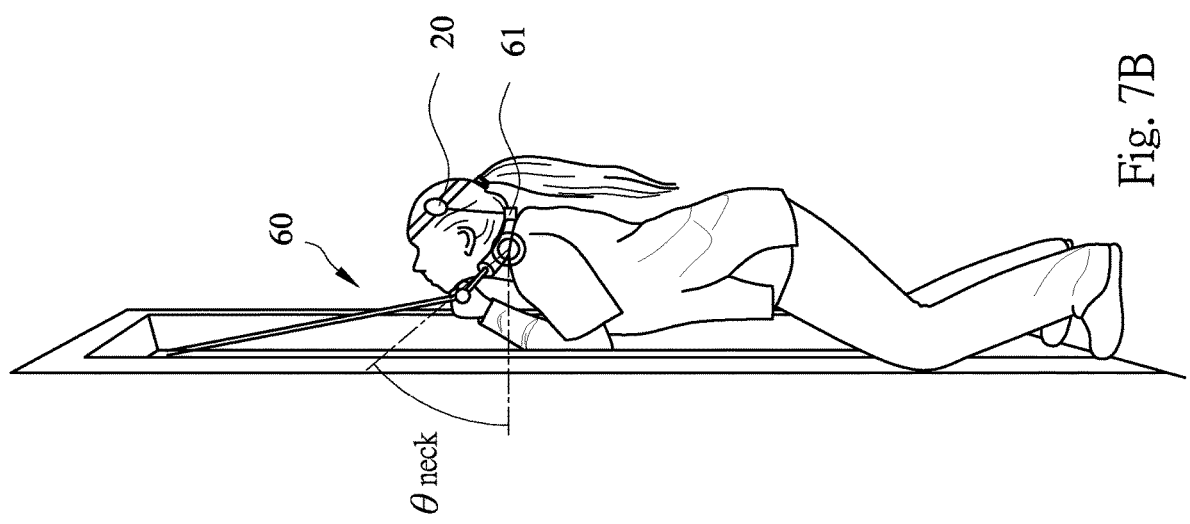

Please refer to FIG. 7A to FIG. 7C, FIG. 7A is a schematic view of a cervical spine stretching rehabilitation device according to embodiment 3 of the present invention; and FIG. 7B to FIG. 7C are schematic views of the use of the cervical spine stretching rehabilitation device according to embodiment 3 of the present invention.

As shown in FIG. 7A to FIG. 7C, Example 3 is substantially the same as Example 1, except that the rehabilitation carrier of Example 1 is the lumbar spine swing rehabilitation chair, and the rehabilitation carrier of Example 3 is a cervical spine stretching rehabilitation device 60. In Example 3, the sensing device 20 and a pressure sensor 61 are disposed on a cushion of the cervical spine stretching rehabilitation device 60 to detect the angle and force when the user put his head back. Therefore, it can detect whether the user's action is in place in real time, and can record the number, angle, pressure, time, and date of rehabilitation. In FIG. 7B, $\theta_{neck}$ represents the angle between the chin and the horizontal line, and represents an elevation angle of the user's neck. The cervical spine stretching rehabilitation device 60 is mainly used for assisting in relieving neck and upper back pain and rehabilitating neck mobility. It also helps in rehabilitating and correcting of ligamentum and cervical discs, and restores the naturalness of the neck curve through gentle neck stretching.

Figure 8B:
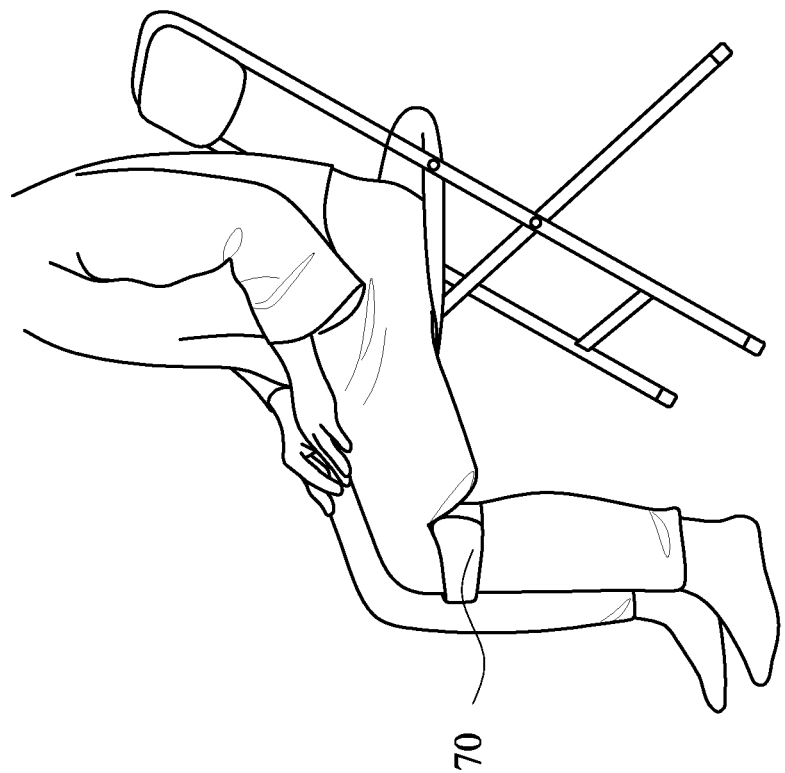
FIG. 8B-FIG. 8D are schematic views of the use of the leg joint rehabilitation belt according to embodiment 4 of the present invention.
Figure 8A:
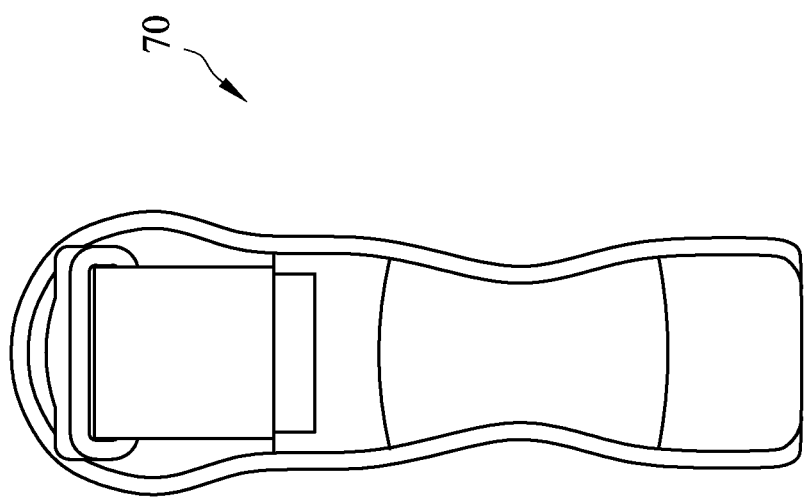
FIG. 8A is a schematic view of a leg joint rehabilitation belt according to embodiment 4 of the present invention.
Figure 8C:
Figure 8D:
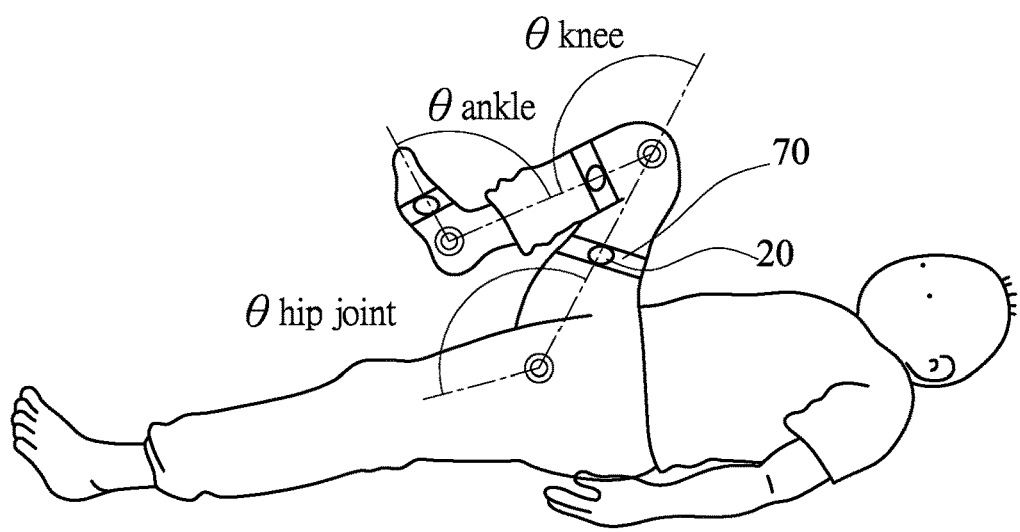

Please refer to FIG. 8A to FIG. 8D, FIG. 8A is a schematic view of a leg joint rehabilitation belt according to embodiment 4 of the present invention; and FIG. 8B-FIG. 8D are schematic views of the use of the leg joint rehabilitation belt according to embodiment 4 of the present invention.

As shown in FIG. 8A to FIG. 8D, Example 4 is substantially the same as Example 1, except that the rehabilitation carrier of Example 1 is the lumbar spine swing rehabilitation chair, and the rehabilitation carrier of Example 4 is a leg joint rehabilitation belt 70. In Example 4, the sensing device 20 is mounted in a strap to detect the leg lift angle of the user. In FIG. 8D, $\theta_{knee}$ represents the angle between the knee and the calf, $\theta_{ankle}$ represents the angle between the ankle and the calf, and $\theta_{hip\ joint}$ represents the angle between the bent foot and the flat foot. The model portrait on the display device 10 will act in synchronization with the user, and give real-time action reminders with sound effects and icons, so that the user can know whether his actions are correct and make adjustments while exercising.

In addition, the action of the model portrait can be projected on the computer or TV through the image output function of the mobile phone to construct a better visual guidance effect or interaction. The display device 10 of the rehabilitation action guidance assist device 1 has a plurality of application programs, and the application programs include a rehabilitation operation course. The rehabilitation operation course is played by playing actual coaching videos or virtual coaching animations to guide the user to correctly perform the rehabilitation action, and displays the action state values 211 on the rehabilitation evaluation system 30 in real time. Therefore, the user can correctly and effectively operate the rehabilitation carrier to achieve the best results of rehabilitation exercise at home or without an instructor through self-training independently. Furthermore, there are three ways to guide and prompt in the rehabilitation action course. First, the rehabilitation action videos with correct standards from qualified physical therapists (PT) are actually recorded. Secondly, the external motion capture captures the actual rehabilitation actions of qualified physical therapists, and then imports the data into the 3D virtual coach model to produce 3D guidance animations. Thirdly, when the user cannot use the video or animation to assist and guide, the voice prompt can be used for doing the rehabilitation course.

In summary, the contents of the rehabilitation exercise course recorded in the display device 10 of the rehabilitation action guidance assist device 1 of the present invention includes the date of use, the length of time, the number of training sessions, the actual exercise data, and the accuracy of the follow-up rehabilitation exercise. Therefore, the user or the physical therapist can understand the rehabilitation effect more clearly with the presentation of the data.

The foregoing description, for the purpose of explanation, has been described with reference to specific embodiments. However, the embodiments were chosen and described in order to best explain the principles of the disclosure and its practical applications, to thereby enable others skilled in the art to best utilize the disclosure and various embodiments with various modifications as are suited to the particular use contemplated. The embodiments depicted above and the appended drawings are exemplary and are not intended to be exhaustive or to limit the scope of the disclosure to the precise forms disclosed. Modifications and variations are possible in view of the above demonstrations.

I claim:

1. A rehabilitation action guidance assistive device, comprising:
    a display device having a user interface that displays an image for a user to watch, wherein the image comprises a demonstration of rehabilitation actions and a model portrait the user to imitate;
    a sensing device disposed on a rehabilitation carrier that comprises a rehabilitation chair adapted to receive the user to sit thereon, wherein the rehabilitation chair comprises a support base having an accommodation space in which a connecting mechanism is mounted to connect a seat cushion on which the user sits to the support base in a movable manner, two cross bars being respectively mounted to and extending from two opposite sides of the support base, two armrests being respectively mounted on and extending upward from the two cross bars, and wherein the sensing device is mounted to an underside of the seat cushion, and wherein the sensing device comprises:
    a sensing element comprising an inertial measurement unit operable to detect a movement of the seat cushion caused by the user sitting thereon by following the image displayed on the user interface of the display device, so as to generate action state values of the user sitting on the seat cushion of the rehabilitation chair;
    a storage element installed in the sensing device and electrically connected to the sensing element to receive and store the action state values generated by the sensing element;
    a processing element installed in the sensing device and electrically connected to the storage element for receiving and processing the action state values stored in the storage element for comparison with a preset value to selectively issue a warning signal;
    a data transmission element installed in the sensing device and electrically connected to the processing element to transmit the action state values to a rehabilitation evaluation system through a wireless communication arrangement; and
    a power supply element installed in the sensing device and electrically connected to the sensing element, the storage element, the processing element and the data transmission element, so as to provide an electric power for operation of the sensing device;
    wherein the rehabilitation evaluation system is installed in the display device to receive the action state values transmitted through the data transmission element, and the rehabilitation evaluation system is operable to indicate a difference between the action state values and reference action state values of the model portrait of the image displayed on the user interface;
    wherein the action state values and the reference action state values are a sequence of numbers of a X-axis, a Y-axis and a Z-axis represented by a time series sequence, the X-axis is a left and right direction relative to a human body, the Y-axis is a front and back direction relative to the human body, the Z-axis is an up and down direction of the human body; a following error value of the time series sequence is calculated, an error angle value is calculated through a calculation of a trigonometric function equation, and an average error angle is obtained by following equations;

$[Gx(k)'Gy(k)'Gz(k)]_{ref}$, $K=1\ldots n$, it represents the reference action state values of the model portrait at $Tk$;

$[Gx(k)'Gy(k)'Gz(k)]_{act}$, $K=1\ldots n$, it represents the user's action state values at $Tk$;

the following error value of the time series sequence is calculated by a following equation;

the following error value $(k)=\sqrt{[Gx(k)_{ref}-Gx(k)_{act}]^2+[Gy(k)_{ref}-Gy(k)_{act}]^2+[Gz(k)_{ref}-Gz(k)_{act}]^2}$;

the error angle value is calculated through the calculation of trigonometric function equation, and an average error angle is obtained by following equations;

ErrorAngle$(k)$=Error$(k)/G*(180/Pi)$

Average Error Angle=$\Sigma$Error Angle$(k)/n$ $k=1\ldots n$;

when the average error angle is less than 10 degrees, it means that a user's rehabilitation action is correct; when the average error angle is between 10 degrees and 20 degrees, it means that the user's rehabilitation action is acceptable; and when the average error angle is between 20 degrees and 30 degrees, it means that the user's rehabilitation action needs to be reviewed and corrected.

2. The rehabilitation action guidance assistive device in claim 1, wherein the action state values are acceleration values, rotation angular velocity values of the rehabilitation carrier or the user, or a linear velocity of the rehabilitation carrier or body parts after the signal calculation based on the acceleration values and the rotation angular velocity values, positions of the rehabilitation carrier or the body parts or posture angles of the rehabilitation carrier or the body parts.

3. The rehabilitation action guidance assistive device in claim 1, wherein the inertial measurement unit is composed of a triaxial accelerometer, or a combination of a three-axis gyro and the triaxial accelerometer, or a combination of the three-axis gyro, the triaxial accelerometer and a three-axis geomagnetometer.

4. The rehabilitation action guidance assistive device in claim 1, wherein when the processing element determines that the warning signal needs to be sent out, it triggers a warning element to send out the warning signal; simultaneously, the data transmission element sends the warning signal to the display device so that the user interface displays the warning signal, and the warning element is a buzzer or a vibrator.

5. The rehabilitation action guidance assistive device in claim 1, wherein the processing element further comprises a timer and a counter; the timer is used for calculating a time length when the sensing element is operated; and the sensing element transmits swing signals from the rehabilitation carrier or the user to the counter, so that the counter records the swing signals of the rehabilitation carrier or the user as a frequency signal; the time length and the frequency signal are transmitted to the storage element, and the time length and the frequency signal are transmitted to the rehabilitation evaluation system through the processing element and the data transmission element.

6. The rehabilitation action guidance assistive device in claim 1, wherein the wireless communication arrangement comprises one of BLUETOOTH® communication protocol, wireless network communication protocol, wireless RF communication, broadband network communication, ZIG-BEE®, THREAD®, 3G® communication protocol or 4G® communication protocol.

* * * * *